US 8,568,383 B2

(12) United States Patent
Sagisaka et al.

(10) Patent No.: US 8,568,383 B2
(45) Date of Patent: Oct. 29, 2013

(54) DISPOSABLE PANTS-TYPE WEARING ARTICLE AND METHOD FOR MAKING THE SAME

(75) Inventors: Minako Sagisaka, Kagawa (JP); Takayuki Miyoshi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 540 days.

(21) Appl. No.: 12/746,714

(22) PCT Filed: Aug. 15, 2008

(86) PCT No.: PCT/JP2008/064654
§ 371 (c)(1),
(2), (4) Date: Sep. 11, 2010

(87) PCT Pub. No.: WO2009/072326
PCT Pub. Date: Jun. 11, 2009

(65) Prior Publication Data
US 2010/0324524 A1    Dec. 23, 2010

(30) Foreign Application Priority Data

Dec. 7, 2007   (JP) ................................. 2007-317577

(51) Int. Cl.
*A61F 13/15*    (2006.01)
(52) U.S. Cl.
USPC ................................. 604/385.25; 604/385.24
(58) Field of Classification Search
USPC ........................ 604/385.25, 385.26, 385.28
See application file for complete search history.

(56) References Cited

U.S. PATENT DOCUMENTS

| 4,743,241 A | 5/1988 | Igaue et al. |
| 6,306,122 B1 * | 10/2001 | Narawa et al. ............. 604/385.3 |
| 6,939,334 B2 * | 9/2005 | Odorzynski et al. ...... 604/385.24 |
| 7,094,227 B2 * | 8/2006 | Ishiguro et al. .......... 604/385.25 |
| 7,159,831 B2 * | 1/2007 | Gartner et al. ............. 248/274.1 |
| 2001/0003153 A1 | 6/2001 | Sayama et al. |
| 2003/0078556 A1 * | 4/2003 | Sasaki et al. ............. 604/385.25 |
| 2003/0083638 A1 * | 5/2003 | Molee ...................... 604/385.27 |
| 2005/0004548 A1 * | 1/2005 | Otsubo et al. ............ 604/385.25 |

FOREIGN PATENT DOCUMENTS

| JP | 62243806 A | 10/1987 |
| JP | 03-082467 A | 4/1991 |
| JP | 07-163617 A | 6/1995 |
| JP | 2000-279444 A | 10/2000 |
| JP | 2001149409 A | 6/2001 |

OTHER PUBLICATIONS

ISR for PCT/JP2008/064654, mailed Nov. 25, 2008.

* cited by examiner

*Primary Examiner* — Lynne Anderson
(74) *Attorney, Agent, or Firm* — Lowe Hauptman & Ham, LLP (57) ABSTRACT

The present invention provides a disposable pants-type wearing article improved so as to eliminate a possibility that elastic members attached to peripheral edges of respective leg-openings might irritate the wearer's skin. The disposable pants-type wearing article has a band-like elastic member having a width dimension in a range of 5 to 60 mm and extending along peripheral edges of leg-openings so as to go half around each of the leg-openings. The elastic member comprises opposite end segments each lying in the uppermost zone of the leg-opening, a middle segment lying in the lowermost zone of the leg-opening and extending across a crotch region and intermediate segments each extending between the associated end segment and the middle segment wherein the intermediate segments are not bonded to sheet material constituting the wearing article.

11 Claims, 8 Drawing Sheets

DISPOSABLE PANTS-TYPE WEARING ARTICLE AND METHOD FOR MAKING THE SAME

RELATED APPLICATIONS

The present application is national phase of International Application Number PCT/JP2008/064654, filed Aug. 15, 2008, and claims priority from, Japanese Application Number 2007-317577, filed Dec. 7, 2007, the disclosures of which are hereby incorporated by reference herein in their entirety.

TECHNICAL FIELD

The present invention relates to a disposable pants-type wearing article and more particularly to such pants-type wearing article provided along peripheral edges of respective leg-openings with belt-like elastic members.

RELATED ART

In the disposable pants-type diaper as an example of the disposable pants-type wearing article, it is well known to attach a plurality of rubber threads under tension to the peripheral edges of the respective leg-openings and thereby to make these peripheral edges elastically tensile. Such pants-type wearing article is disclosed, for example, in Japanese Patent Application Laid-Open Publication No. 1991-82467 (PATENT DOCUMENT 1) according to which the thread-like elastic members are attached under tension to the inner surface of the top-sheet and/or the back-sheet by adhesive so as to extend along the peripheral edges of the respective leg-openings in arcs.

The disposable liquid-absorbent pants disclosed in Japanese Patent Application Laid-Open Publication No. 1987-243806 (PATENT DOCUMENT 2) are provided in the vicinity of the leg-openings with the belt-like elastic members each having a width in a range of 10 to 45 mm extending in front-rear direction of the pants and the belt-like elastic members each having a width in a range of 10 to 45 mm extending in a transverse direction of the pants.

PATENT DOCUMENT 1: Japanese Patent Application Laid-Open Publication No. 1991-82567
PATENT DOCUMENT 2: Japanese Patent Application Laid-Open Publication No. 1987-243806

DISCLOSURE OF THE INVENTION

Problem to be Solved by the Invention

When it is tried to attach thread-like elastic members under tension to the wearing article along the peripheral edges of the respective leg-openings as the wearing article disclosed in Japanese Patent Application Laid-Open Publication No. 1991-82567 is the case, quantity of coating per unit area of adhesive used for this purpose must be relatively large to prevent these elastic members from falling off from between the top- and back-sheets in the course of repetitive stretch and contraction. However, after the wearing article has been coated with a large quantity of adhesive at a low degree of viscosity, cure of adhesive undesirably stiffens the regions of the top-sheet and/or the back-sheet in which the elastic members are bonded to the wearing article. In consequence, there is possibility that the wearer's skin in contact with these stiffened regions might be uncomfortably irritated these stiffened regions at every moment the elastic members are repetitively stretched and contracted.

In the case of the pants disclosed in Japanese Patent Application Laid-Open Publication No. 1987-243806, the belt like elastic members each having a relatively large width dimension are used as the elastic members and consequently it is not apprehended that these elastic members might fall off from between the top- and back-sheets without increasing the quantity of adhesion. However, this PATENT DOCUMENT contains no description of how to handle these belt-like elastic members in the course of continuously producing the pants.

In view of the problems as have been described above, it is a principal object of the present invention to improve the disposable pants-type wearing article and the method for making the same of prior art so as to eliminate possibility that the elastic members attached to the article along the peripheral edges of the respective leg-openings might uncomfortably irritate the wearer's skin.

Measure to Solve the Problem

The present invention intends to achieve the object set forth above includes a first aspect relating to the disposable pants-type wearing article and a second aspect relating to the method for making the same.

The object set forth above is achieved, according to the first aspect of the present invention, by an improvement in a disposable pants-type wearing article having a front-to-rear direction, a transverse direction and a longitudinal direction being orthogonal one to another, and comprising a crotch region, a front waist region extending forward from the crotch region and a rear waist region extending rearward from the crotch region, the front and rear waist regions cooperating together to define a waist-opening while the front and rear waist regions cooperate with the crotch region to define a pair of leg-openings, respective peripheral edges of the leg-openings being at least along portions thereof elastically stretchable and contractible in circumferential directions of the respective openings under an effect of an elastic member.

The improvement according to the first aspect of the invention is characterized in that the elastic member comprises a belt having inner and outer surfaces with respect to the disposable pants-type wearing article and a width in a range of 5 to 60 mm, the belt having leg-contacting segments each extending from a bottom of the leg-opening to a top of the leg-opening so as to go half around each of the wearer's legs, a middle segment extending on the bottom across the crotch region to respective the leg-contacting segments and end segments lying on respective the tops of the leg-openings and fixed to sheet material constituting the wearing article, the middle segment being fixed to the sheet material constituting the wearing article in the crotch region and intermediate segments defined between the end segments and the middle segments being free to be stretched and contracted, wherein the belt is in any one of states (a), (b) and (c) as will be described below:

(a) the middle segment is neither joined nor bonded to the sheet material;

(b) the belt is bonded to the sheet material constituting the wearing article by hot melt adhesive and an application amount of the hot melt adhesive per unit area of the belt is higher in the end segments and the middle segment than in the intermediate segments; and (c) the front waist region and the rear waist region have joint zones extending along opposite side edges of the wearing article, in which these two waist regions are put flat and welded together, the end segments of the belt extend and welded to said joint zones and an application amount per unit area of the belt of hot melt adhesive used to bond the belt and the sheet material to each other is higher in the middle segment than in the intermediate segments.

According to another preferred embodiment of the invention on the first aspect thereof, the front and rear waist regions are elastically stretchable and contractible in the transverse direction in the vicinity of the respective tops of the leg-openings.

According to yet another preferred embodiment of the invention on the first aspect thereof, the belt has the end segments and the middle segment fixed to the sheet material in a manner that the end segments and the middle segment can no more contract.

According to still another preferred embodiment of the invention on the first aspect thereof, the crotch region is provided on its inner side with a panel-like bodily fluid absorbent structure extending in the front-to-rear direction, the bodily fluid absorbent structure is formed along its opposite side edges extending in the front-to-rear direction with leak-proof barriers being elastically stretchable and contractible in the front-to-rear direction, and the leak-proof barriers raise themselves with respect to the inner surface of the bodily fluid absorbent structure so as to prevent any amount of bodily fluids from leaking out through the leg-openings.

According to further another preferred embodiment of the invention on the first aspect thereof, the leg-contacting segment in the belt is any one of a front leg-contacting segment extending, in a front half of the crotch region, from the middle segment along the periphery of the leg-opening to the top and a rear leg-contacting segment extending, in a rear half of the crotch region, from the middle segment along the periphery of the leg-opening to the top.

The object set forth above is achieved, according to the second aspect of the present invention, by an improvement in a method for continuously making a disposable pants-type wearing article having a front-to-rear direction, a transverse direction and a longitudinal direction being orthogonal one to another, and comprising a crotch region, a front waist region extending forward from the crotch region and a rear waist region extending rearward from the crotch region, the front and rear waist regions cooperating together to define a waist-opening while the front and rear waist regions cooperate with the crotch region to define a pair of leg-openings, respective peripheral edges of the leg-openings being at least along portions thereof elastically stretchable and contractible in circumferential directions of the respective openings under an effect of an elastic member wherein the method is defined by a mechanical direction and a cross direction orthogonal to the mechanical direction.

The improvement according to the present invention on the second aspect thereof is characterized in that the method comprises the steps of:

(a) continuously feeding, in the machine direction, a first elastic web which is elastically stretchable and contractible in the machine direction and has upper and lower surfaces extending in the machine direction in parallel to each other as well as first and second side edges extending also in the machine direction in parallel to each other, the first elastic web having a width between the first and second side edges, said width being a dimension in the cross direction in a range of 6 to 60 mm;

(b) coating one of the upper and lower surfaces of the first side edge with first adhesive intermittently in a predetermined cycle;

(c) coating one of the upper and lower of the second side edge with second adhesive intermittently in the same cycle as that in which said first side edge is coated with the first adhesive but with a shift of half cycle and each segment of the second adhesive is spaced from each segment of the first adhesive by a predetermined distance as measured in the machine direction and has a dimension as measured in the cross direction adjusted so that a total dimension of the first and second adhesive segments as measured in the cross direction do not exceed the width of the first elastic web;

(d) continuously feeding a first inelastic web having upper and lower surfaces together with a second inelastic web having upper and lower surfaces in the machine direction, then placing one of the upper and lower surfaces of the first inelastic web in contact with the first adhesive but not in contact with the second adhesive to bond the first inelastic web to the first elastic web while placing one of the inner and outer surfaces of the second inelastic web in contact with the second adhesive but not in contact with the first adhesive to bond the second inelastic web to the first elastic web and thereby to obtain a first composite web;

(e) broadening the first composite web in the cross direction with the first and second inelastic webs being held and thereby elastically stretching the first elastic web between the first adhesive and the second adhesive adjacent to each other a pair of the adjacent in the cross direction;

(f) continuously feeding, in the machine direction, a third inelastic web having a dimension in the cross direction larger than the dimension by which the first adhesive and the second adhesive are spaced from each other in the cross direction and upper and lower surfaces toward the broadened first composite web to place and bond the third inelastic web on and to the first inelastic web and the second inelastic web and to obtain second composite web;

(g) continuously feeding, in the machine direction, a second and third elastic webs each being elastically stretchable and contractible in the machine direction and having upper and lower surfaces and bonding the second elastic web under tension with one of the upper and lower surfaces to the second inelastic web to obtain third composite web;

(h) cutting the third composite web along an annular guide line being symmetric about a first center line extending in the cross direction so as to bisect a dimension between the paired adjacent first adhesive zones and extending along the first elastic web on both sides of the first center line and further extending in the cross direction across a second center line to obtain a fourth composite web;

(i) folding back the fourth composite web along the second center line;

(j) forming the fourth composite web with a joint line so that respective halves of the fourth composite web having been folded back may be joined or bonded to each other along the first center line; and (k) cutting the fourth composite web having been folded in the respective halves which have been bonded to each other along the joint line to obtain individual pants-type wearing articles from the fourth composite web.

According to one preferred embodiment of the invention on the second aspect thereof, the method further including, before or after the step (h), a step of bonding the bodily fluid absorbent structure comprising a bodily fluid absorbent core sandwiched between a liquid-pervious sheet and a liquid-impervious sheet to the third composite web in a manner that the liquid-impervious sheet faces the third composite web.

According to another preferred embodiment of the invention on the second aspect thereof, the method further includes a step of coating one of the upper and lower surfaces of the first elastic web with the first adhesive and the second adhesive.

According to still another preferred embodiment of the invention on the second aspect thereof, the method further includes a step of coating one of the upper and lower surfaces of the first elastic web with the first adhesive and coating the other surface with the second adhesive.

According to yet another preferred embodiment of the invention on the second aspect thereof, one of the first and second inelastic webs has a width broadened in the cross direction across the first adhesive and the second adhesive in the first composite web after broadened and the third inelastic web lying on the side opposite to the one inelastic web with respect to the first elastic web.

Effect of the Invention

Concerning the first aspect of the present invention, the leg elastic member for the disposable pants-type wearing article comprises the belt having a width in a range of 5 to 60 mm and comprises the leg-contacting segments linearly extending from the bottom of the leg-openings and the middle segment extending across the crotch region at the bottom of the leg-openings wherein the intermediate segments extend under tension between the end segments of the respective leg-contacting segments and the middle segment. The middle segment of the belt may be fully left free from the wearing article or, if the middle segment must be bonded to the wearing article, it is not required to use a large amount of adhesive to firmly bond the middle segment to the wearing article. Consequentially, it is not apprehended that the middle segment might irritate the wearer's skin even when this middle segment is stretched or contracted.

In the method for making the disposable pants-type wearing article according to the present invention on the second aspect of thereof, the first inelastic web is bonded to the first side edge of the first elastic web by first adhesive while the second inelastic web is bonded to the second side edge by second adhesive to obtain the first composite web and then the first composite web is elastically broadened in the cross direction with these first and second inelastic webs being held. In consequence, the portion of the first elastic web defined between the first adhesive and the second adhesive is stretched in the cross direction and extends, as a whole, in the machine direction in zigzag pattern. The first elastic web may be partially laid in front or rear half of the crotch region to make it possible to attach the belt-like leg elastic member to the peripheral edges of the respective leg-openings of the pants-type wearing articles continuously made.

DESCRIPTION OF THE BEST MODE FOR WORKING OF THE INVENTION

Details of the disposable pants-type wearing article and the method for making the same will be more fully understood from the following description given hereunder in reference to the accompanying drawings.

Figure 1:
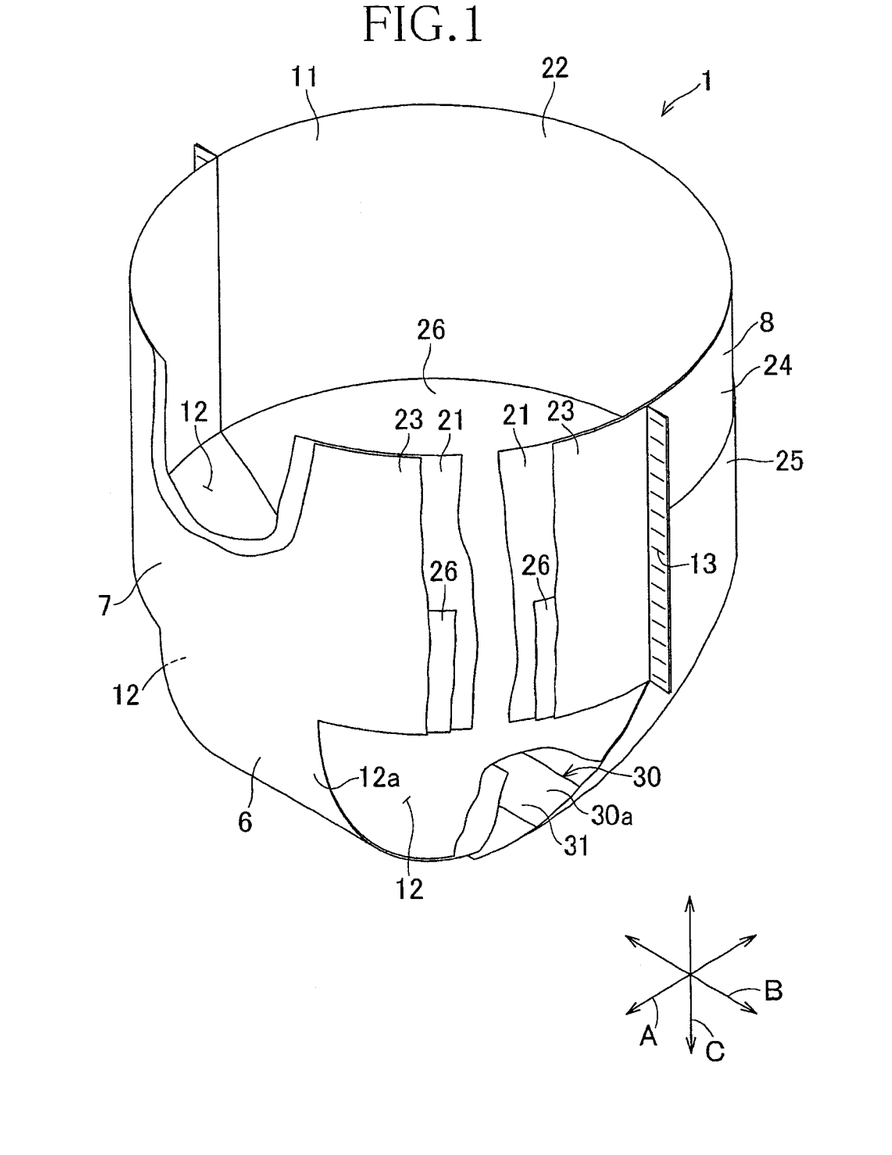
FIG. 1 is a perspective view showing the pants with the front waist region partially cutaway.
Figure 2:
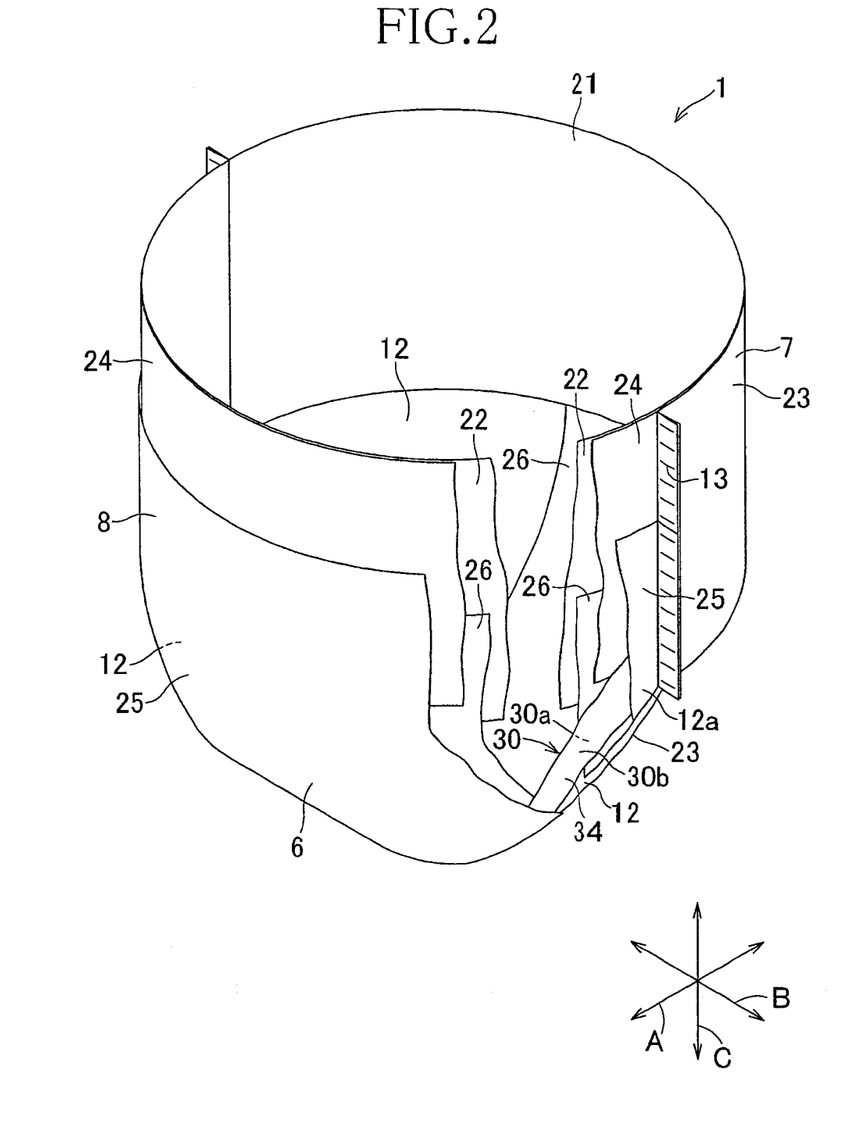
FIG. 2 is a perspective view showing the pants with the rear waist region partially cutaway.

FIGS. 1 and 2 are partially cutaway perspective view of disposable pants as a typical example of the disposable pants-type wearing article wherein FIG. 1 shows a front waist region 7 as partially broken away and FIG. 2 shows a rear waist region 8 as partially broken away. In FIGS. 1 and 2, a front-rear direction, a transverse direction and a vertical direction are indicated by double-headed arrows A, B and C, respectively.

The pants 1 have a crotch region 6 curved in the front-to-rear direction A, a front waist region 7 extending forward from the crotch region 6 and a rear waist region 8 extending rearward from the crotch region 6. Each of the front and rear waist regions 7, 8 has a pair of opposite side edges put flat and joined together in joint zones 13 arranged along these side edges 13 and thereby a waist-opening 11 is defined. At the same time, the front and rear waist regions 7, 8 and the crotch region 6 cooperate one with another to define a pair of leg-openings 12. Respective inner surfaces of the front and rear waist regions 7, 8 are defined by elastic non-woven fabric sheets 21, 22 which elastically stretch and contract so as to make the front and rear waist regions 7, 8 elastically fit to the wearer's waist. Respective outer surfaces of the front and rear waist regions 7, 8 are defined by inelastic non-woven fabric sheets 23, 24. Outer surface of the crotch region 6 is defined by the inelastic non-woven fabric sheet continuously extending from the front waist region 7 and an inelastic non-woven fabric 25 partially overlapping this inelastic non-woven fabric sheet 23. The inelastic non-woven fabric sheet 25 extends from the crotch region 6 to the rear waist region 8 and partially overlaps the inelastic non-woven fabric sheet 24. In the crotch region 6 of FIG. 2, a strip-shaped leg elastic member 30 extends along a peripheral edge 12a of the leg-opening 12 so as to extend substantially half around the leg-opening 12. It should be understood here that the expression "elastic non-woven fabric" refers to the non-woven fabric able to be elastically stretched and contracted in a repetitive manner during use of the pants 1 while the expression "inelastic non-woven fabric" refers to the non-woven fabric unable to be elastically stretched and contracted in a repetitive manner during use of the pants 1, for example, unable to be elastically stretched, or able to be stretched but unable to be contracted substantially to the initial dimension.

Figure 3:
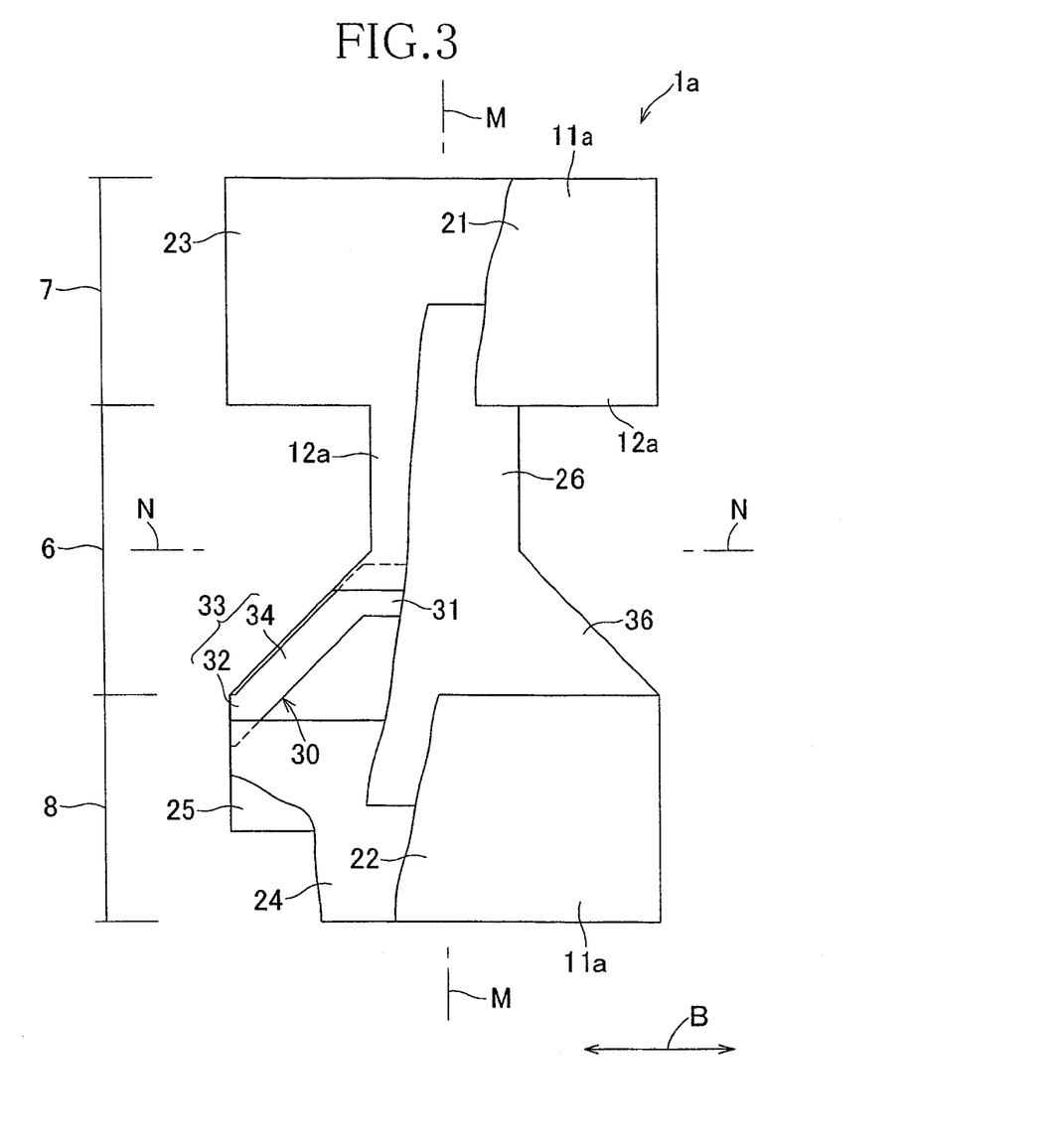
FIG. 3 is a partially cutaway plan view of a prototype of the pants.

FIG. 3 is a partially cutaway plan view of a prototype 1a of the pants 1 wherein the crotch region 6 as well as the front and rear waist regions 7, 8 have been developed in the front-to-rear direction A as well as in the transverse direction B as viewed in FIGS. 1 and 2. The components common to the pants 1 and the prototype 1a are designated with the reference numerals similar to those used in the pants 1. A dimension of the prototype 1a in the transverse direction B is bisected by a center line M-M and a dimension thereof in the front-to-rear direction A is bisected by a center line N-N. In the prototype 1a, the inner surface of the crotch region 6 is defined by inelastic non-woven fabric sheet 26. This inelastic non-woven fabric sheet 26 extends into the front and rear waist regions 7, 8 and, in the front waist region 7, the inelastic non-woven fabric sheet 26 is sandwiched between the elastic non-woven fabric sheet 21 and the inelastic non-woven fabric sheet 23 and joined to at least one of these non-woven fabric sheets 22, 23 by adhesion or sealing. In the rear waist region 8, the inelastic non-woven fabric sheet 26 is sandwiched between the elastic non-woven fabric sheet 22 and the inelastic non-woven fabric sheet 224 and joined to at least one of these non-woven fabric sheets 222, 224 by adhesion or sealing. In a rear half 36 of the crotch region 6, the leg elastic member 30 extends so as to describe an inverted V-shape. The elastic non-woven fabric sheet 21 joined to the inelastic non-woven fabric sheets 23, 26 in the manner as has been described above and the elastic non-woven fabric sheet 22 joined to the inelastic non-woven fabric sheets 24, 26 in the manner as has been described above are joined under tension in the transverse direction B to these inelastic non-woven fabric sheets 23, 24, 26.

The leg elastic member 30 is in the form of belt having inner and outer surfaces 30a, 30b with respect to the pants 1 and comprises a middle segment 31 extending in parallel to the center line N-N across the crotch region 6 at the lowermost zone thereof, extremely short opposite end segments 32 in parallel to the center line N-N and intermediate segments extending between the middle segment 31 and the respective end segments 32 so as to intersect the center line N-N. The middle segment 31 and the end segments 32 are permanently bonded to at least the inelastic non-woven fabric sheets 23, 24 of the inelastic non-woven fabric sheets 23, 24, 25, 26 overlapping the middle segment 31 and the end segments 32 preferably so that these segments 31, 32 could not be peeled off from these inelastic non-woven fabric sheets 23, 24. The intermediate segment 34 extends at least partially along the peripheries 12a of the leg-openings 12 (See FIGS. 1 and 2 also) and is elastically stretched and contracted during use of the pants 1 so as to make the peripheries 12a elastically fit around the wearer's legs.

Such intermediate segment 34 may not be bonded to the inelastic non-woven fabric sheets 25, 26 which are in contact with this intermediate segment 34 or may be bonded thereto by an extremely small amount of hot melt adhesive. If the intermediate segment 34 and the inelastic non-woven fabric sheets 25, 26 are not bonded together, there is no anxiety that the inelastic non-woven fabric sheets 25, 26 might be at least partially hardened and irritate the wearer's skin as the intermediate segment 34 and the inelastic non-woven fabric sheets 25, 26 bonded together are the case. If the intermediate segment 34 and the inelastic non-woven fabric sheets 25, 26 are bonded together by an extremely small amount of hot melt adhesive, a degree at which the inelastic non-woven fabric sheets 25, 26 may be hardened by hot melt adhesive is generally low, for example, so far as the one surface of the intermediate segment 34 is intermittently coated with about 3 to 20 g/m2 of hot melt adhesive. In this way, with the pants 1 having such intermediate segment 34, it is not apprehended that, even if the inelastic non-woven fabric sheets 25, 26 rub the wearer's skin under stretching or contraction of the intermediate segment 34, the wearer's skin might be uncomfortably irritated thereby.

Referring to FIG. 3, in the front waist region 7 of the prototype 1a, the elastic non-woven fabric sheet 21 extends so as to define a peripheral edge 11a of the waist-opening 11 and the peripheral edges 12a of the leg-openings 12 in the front waist region 7 and bonded under elastic tension in the transverse direction B to the inelastic non-woven fabric sheets 23, 26. Such elastic non-woven fabric sheet 21 serves as so-called waist elastic member making the peripheral edge 11a of the waist-opening 11 elastically fit around the wearer's waist and, at the same time, serves as so-called leg elastic member making the peripheral edges of the leg-openings 12 elastically fit around the wearer's legs. In the rear waist region 8, the elastic non-woven fabric sheet 22 extends so as to define the peripheral edge 11a of the waist-opening 11 and is bonded under elastic tension in the transverse direction B to the inelastic non-woven fabric sheets 24, 26.

In the pant 1, the elastic non-woven fabric sheets 21, 22 respectively may comprise elastic strings such as polyurethane elastic strings which are elastically stretchable and contractible. Each of such elastic strings contains, in turn, elastically stretchable and contractible crimped composite fiber. The inelastically stretchable non-woven fabric sheets 21, 22 may be made also by laminating an inelastically stretchable non-woven fabric sheet with elastic film of thermoplastic elastomer or the like. As the inelastic non-woven fabric sheets 23, 24, 25, 26, spun bond non-woven fabric, melt bond non-woven fabric, air-through non-woven fabric, spun lace non-woven fabric or the like may be used. In addition, the inelastic non-woven fabric sheet containing natural fiber such as cotton fiber or rayon fiber or semi-synthetic fiber may be used as these inelastic non-woven fabric sheets 23, 24, 25, 26. It is also possible in the pants 1 to replace the elastic non-woven fabric 21, 22 by elastically stretchable plastic film and/or to attach, in addition, thread-like or belt-like elastic members to the peripheral edge 11a of the waist-opening 11 and thereby to enhance contractile force of the peripheral edge 11a. It is also possible to replace the inelastic non-woven fabric 23, 24, 25, 26 by inelastic plastic film. If the inelastic non-woven fabric 26 or the inelastic plastic film replacing the non-woven fabric 26 is liquid-impervious, the crotch region 6 also will be liquid-impervious.

Figure 4:
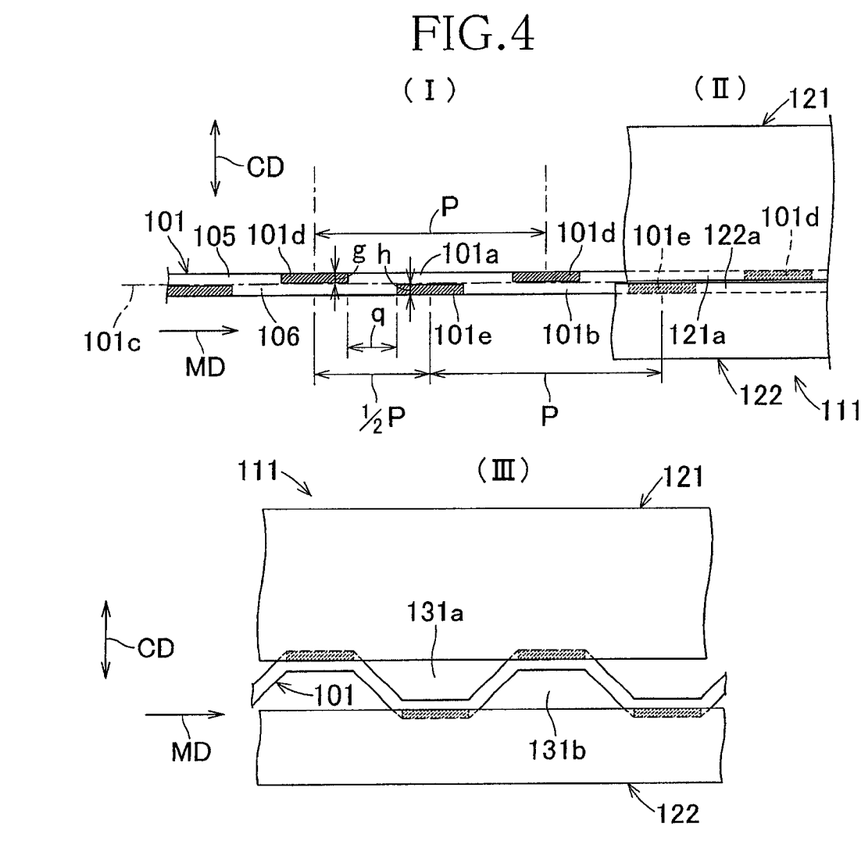
FIG. 4 is a schematic diagram exemplarily illustrating the method for making the pants.
Figure 5:
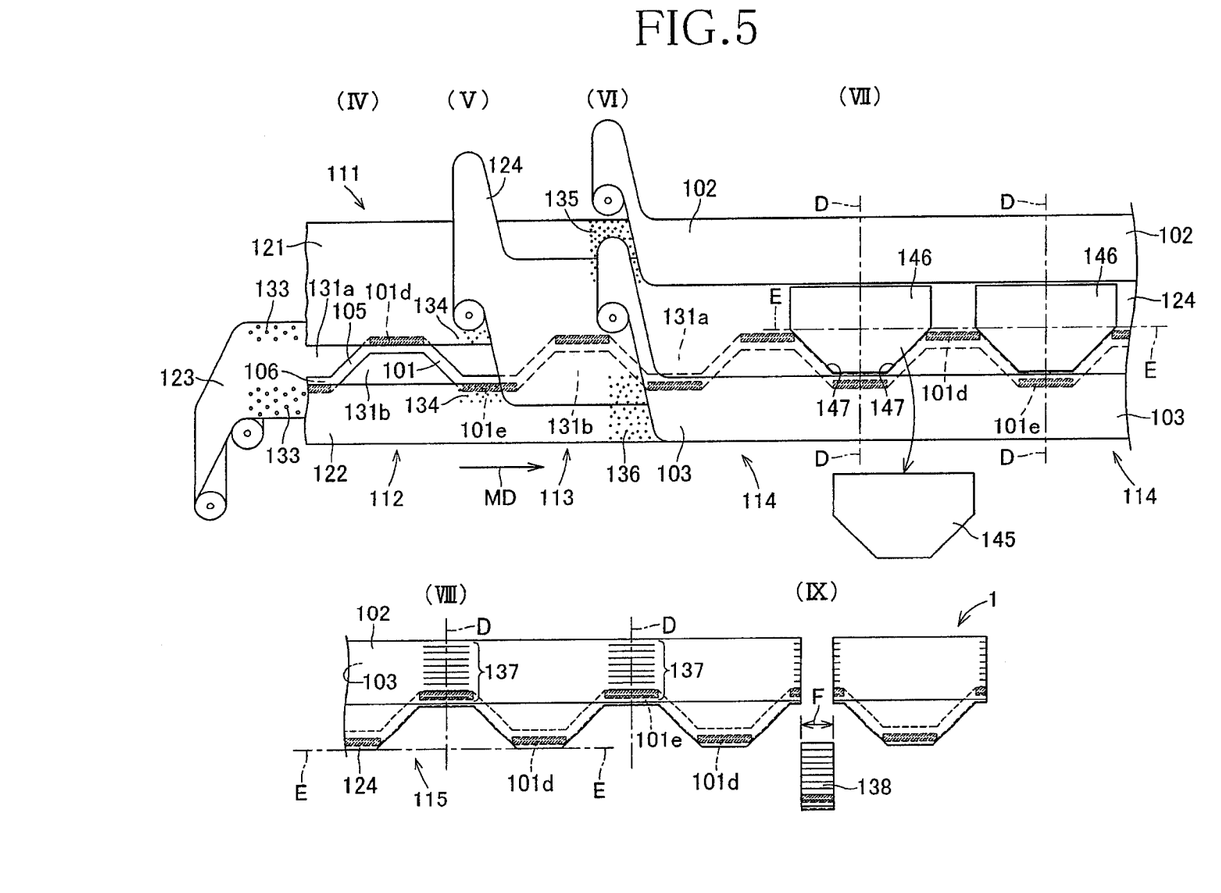
FIG. 5 is a schematic diagram illustrating steps following the steps illustrated by FIG. 4.

FIGS. 4 and 5 are schematic diagrams exemplarily illustrating the method for making the pants wherein a machine direction and a direction which is orthogonal to the machine direction are designated by MD and CD, respectively.

In a first step I of the process illustrated by FIG. 4, an elastically stretchable and contractible first elastic web 101 is continuously fed in a machine direction MD. The first elastic web 101 has upper and lower surfaces 105, 106 and first and second side edges 101a, 101b wherein a dimension, i.e., a width of the first elastic web 101 as measured in a cross direction CD is bisected by a center line 101c. In the step I also, the upper surface 105 of the first elastic web 101 is coated along the first side edge 101a at a predetermined period p with first hot melt adhesive 101d while the upper surface 105 is coated along the second side edge 101b at the same predetermined period p but shifted by ½ p with second hot melt adhesive 101e. The first adhesive 101d and the second adhesive 101e are spaced from each other by a dimension q in the machine direction MD. A sum of a dimension g of the first adhesive 101d and a dimension h of the second adhesive 101e each measured in the cross section CD should be adjusted so as not to exceed the width of the first elastic web 101.

In a second step II of the process illustrated by FIG. 4, a first inelastic web 121 is continuously fed in the machine direction MD and an inner side edge 121a of the first inelastic web 121 is bonded to the first elastic web 101 by the first adhesive 101d. At the same time, a second inelastic web 122 is continuously fed in the machine direction MD and an inner side edge 122a of the second inelastic web 122 is bonded to the first elastic web 101 by the second adhesive 101e. The first inelastic web 121 is fed so as not to overlap the second adhesive 101e and the second inelastic web 122 is fed so as not to overlap the first adhesive 101d. In the second step II, in this way, a first composite web 111 is obtained, which comprises the first elastic web 101, the first inelastic web 121 and the second inelastic web 122.

In a third step III of the process illustrated by FIG. 4, the first inelastic web 121 and the second inelastic web 122 constituting the first composite web 111 is respectively held and pulled apart in the cross direction CD to broaden the first composite web 111. The first elastic web 101 is deformed thereby and extends in the machine direction MD in zigzag pattern so that substantially trapezoidal apertures 131a, 131b are defined alternately in the machine direction MD between the first elastic web 101 and the first inelastic web 121 as well as between the first elastic web 101 and the second inelastic web 102.

In a fourth step IV of the process illustrated by FIG. 5, a third inelastic web 123 is continuously fed in the machine direction MD and bonded to the first and second inelastic webs 121, 122 constituting the broadened first composite web 111 by third hot melt adhesive 133 to obtain a second composite web 112 having the apertures 131a, 131b closed by the third inelastic web 123. While it is possible to bond the third inelastic web 123 to the first composite web 111 either from the upper surface 105 or from the lower surface 106 of the first elastic web 101, it is preferred to bond the third inelastic web 123 to the first composite web 111 from the side of the lower surface 106 of the first elastic web 101 so that the first elastic web 101 is sandwiched between the first and second inelastic webs 121, 122, on one hand, and the third elastic web 123 it is preferred to bond the third inelastic web 123 to the first composite web 111 from the side of the lower surface 106 of the first elastic web 101, as illustrated, so that the first elastic web 101 is sandwiched between the first and second inelastic webs 121, 122, on one hand, and the third elastic web 123, on the other hand. A range in which the third adhesive 133 is applied may be broadened to bond the third inelastic web 123 to the first elastic web 101. It should be understood that, illustrating of a step IV and the subsequent steps, among those overlapping one another and being invisible in the diagrams, only the first elastic web 101 is indicated by chain lines to clarify its presence.

In a fifth step V of the process illustrated by FIG. 5, a fourth inelastic web 124 is continuously fed in the machine direction MD and bonded to the first and second inelastic webs 121, 122 constituting the second composite web 112 by fourth hot melt adhesive 134 so that the first elastic web 101 may be sandwiched between the fourth inelastic web 124 and the third inelastic web 123. In this way, a third composite web 113 is obtained. A range of application for the fourth adhesive 134 as measured in the cross direction CD may be adjusted to bond the first elastic web 101 and the fourth inelastic web 124 to each other.

In a sixth step VI of the process illustrated by FIG. 5, the second elastic web 102 and third elastic web 103 are continuously fed in the machine direction MD and the second elastic web 102 is bonded to the first inelastic web 121 and the fourth inelastic web 124 by fifth hot melt adhesive 135 while the third elastic web 103 is bonded to the second inelastic web 122 and the fourth inelastic web 124 by sixth hot melt adhesive 136. In this way, fourth composite web 114 is obtained.

In a seventh step VII of the process illustrated by FIG. 5, the portions corresponding to sheets 145, for example, each in a shape as illustrated, of the third and fourth inelastic webs 123, 124 closing the apertures 131a which have been formed in the third step III. In this way, the fourth composite web 114 is formed with through-holes 146. The through-hole 146 is formed so as to be symmetric about a center line bisecting a dimension of the through-hole 146 as measured in the machine direction MD and to have its dimension as measured in the cross direction CD bisected by a center line E-E bisecting the dimension of the fourth composite web 114 as measured in the cross direction CD. Partial segments 147 of peripheral edge defining the through-hole 146 extend along the first elastic member 101. The preferred through-hole 146 is formed between the second elastic web 102 and the third elastic web 103 as viewed in the cross direction CD.

In an eighth step VIII of the process illustrated by FIG. 5, the fourth composite web 114 is folded back along the center line E-E with the second and third elastic webs 102, 103 inside and respective halves of the fourth composite web 114 are joined or bonded together on both sides of the center line D-D by adhesion or sealing. In this way, a fifth composite web 115 having a joint zone 137 is obtained. When the respective halves of the fourth composite web 114 are subjected to sonic sealing to form the joint zone 137, the joint zone 137 may be formed so as to include the first elastic web 101 therein to ensure that the first elastic member 101 is firmly attached with no more any ability of contraction in the joint zone 137, in other words, in the joint zone 13 in FIG. 1.

In a ninth step IX of the process illustrated by FIG. 5, the fifth composite web 115 is cut along the respective center lines D-D so as to bisect the respective joint zones 137 in the machine direction MD to obtain the individual pants-type diapers 200. When the fifth composite web 115 is cut in this manner, the sheets 138 each having an appropriate dimension F in the machine direction MD can be cut away from the fifth composite web 115. In the pants-type diaper 200 obtained in the ninth step IX, the respective elastic members contained therein are illustrated to be under tension.

The first elastic member 101 used in the process as illustrated in FIGS. 4 and 5 is to form a leg elastic member 230 in the crotch region 206 of the pants-type diaper 200 wherein the segment bonded to the first inelastic web 121 by the first adhesive 101d is to define the middle segment 231 of the leg elastic member 230, the segments bonded to the second inelastic web 122 by the second adhesive 101e are to define the both end segments 232 of the leg elastic member 230 in the pants-type diaper 200. The segments of the first elastic member 101 extending under tension in the cross direction CD between the first adhesive 101d and the second adhesive 101e are to define the intermediate segments 234 of the elastic member 230. In a preferred embodiment of the elastic member 230, the middle zone 231 and the end segments 232 bonded to the sheet material in the pants-type diaper 200 by the first adhesive 101d and the second adhesive 101e, respectively, are neither stretchable nor contractible and only the intermediate segments 234 are stretchable and contractible during use of the pants-type diaper 200. To facilitate the intermediate segments 234 to be stretched and contracted, the first elastic member 101 may be left free with respect to the third inelastic web 123 as well as the fourth inelastic web 124. Even if the first elastic member 101 is bonded to any one of these webs 123, 124, the amount of the adhesive to be used is preferably minimized. For example, the hot melt adhesive may be intermittently applied to one surface of the intermediate segments 234 in the order of 3 to 20 g/m² and the first elastic member 101 may be bonded only to the third inelastic web 123 but not to the fourth inelastic web 124. In this way, it is possible not only to reduce the amount of the adhesive to be used but also to eliminate an anxiety that the fourth inelastic web 124 facing the skin of the wearer of the pants-type diaper 200 might be hardened by the hot melt adhesive.

The first elastic web 101 used in the process illustrated by FIGS. 4 and 5 preferably comprises elastic material such as 5 to 60 mm wide belt-like film made of natural rubber, synthetic rubber or thermoplastic elastomer or non-woven fabric containing therein elastic threads such as urethane threads. The second and third elastic webs 102, 103 preferably comprise elastic non-woven fabric containing therein elastic threads such as urethane threads. As the second and third elastic webs 102, 103, such non-woven fabric containing therein rubber threads or rubber belt extending in the machine direction MD may be also used. Furthermore, it is also possible to use elastically stretchable composite non-woven fabric obtained by laminating inelastically stretchable non-woven fabric with elastic plastic film. As the first, second, third and fourth inelastic webs 121, 122, 123, 124, a non-woven fabric or plastic film may be used. While it is possible according to the present invention to obtain the pants-type diaper without any one of the third inelastic web 123 and the fourth inelastic web 124, the pants-type diaper obtained in this manner may sometimes disadvantageously sacrifice the outer appearance of the pants-type diaper as well as the feeling to wear the pants-type diaper due to the first elastic member 101 exposed on the inner or outer surface of the pants-type diaper. The third inelastic web 123 and/or the fourth inelastic web 124 may be formed by opaque material to make the crotch region 206 of the pants-type diaper 200 opaque. While the first elastic web 101 is used on the rear half 236 of the crotch region 206 in the illustrated embodiment, it is also possible to use the first elastic member 101 on the front half of the crotch region 206.

Figure 6:
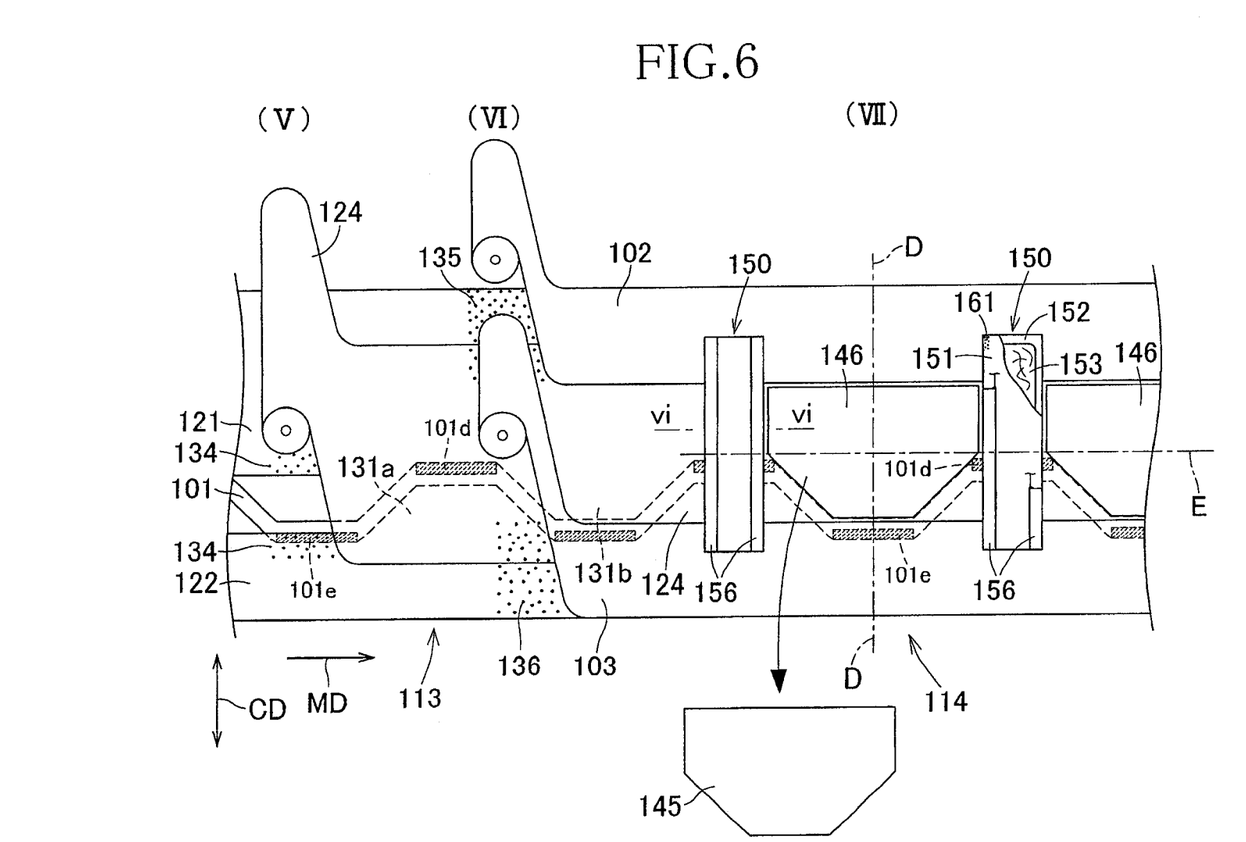
FIG. 6 is a schematic diagram illustrating another example of the method for making the pants.
Figure 7:
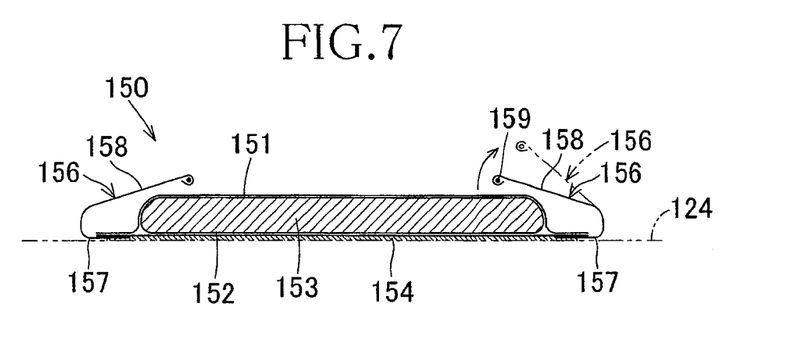
FIG. 7 is a partial sectional view taken along a line vi-vi in FIG. 6.

FIG. 6 is similar to FIG. 5 illustrating the steps V, VI and VII of the method according to one embodiment of the present invention and FIG. 7 is a sectional view taken along a line vi-vi in the seventh step VII in the process illustrated by FIG. 6. Referring to FIG. 6, a bodily fluid absorbent panel 150 is fed to the fourth composite web 114 so as to be placed between each pair of the adjacent through-holes 146. The panel 150 comprises a liquid-pervious topsheet 151, a liquid-impervious backsheet 152 and a bodily fluid absorbent core 153 sandwiched between these two sheets 151, 152. These two sheets 151, 152 extend outward beyond a peripheral edge of the core 153 and put flat and bonded together by hot melt adhesive (not shown) outside the peripheral edge of the core 153 while the backsheet 152 is bonded to the fourth inelastic web 124 as well as the second and third elastic webs 102, 103 constituting the fourth composite web 114 by hot melt adhesive 154. The panel 150 is further provided along its opposite side edges extending in the cross direction CD with leakage barriers 156. In each leakage barrier 156, the one side edge 157 of the liquid-impervious sheet extending in the cross direction CD is bonded to the lower surface of the backsheet 152 and the other side edge 158 includes an elastic member 159 extending in the cross direction CD so that the side edge 158 may raise itself on the topsheet 151 as the elastic member 159 contracts. The side edge 158 has its opposite end portions as viewed in the cross direction CD bonded to the topsheet 151 by hot melt adhesive 161. The pants-type diaper 200 containing such panel 150 is suitable to be used as disposable pants-type diaper or incontinent pants wherein the elastic member 159 contracts as the panel 150 bows in the front-to-rear direction of the crotch region 206 and thereupon the leak-proof barriers 156 raises themselves in the crotch region 206 as indicated by imaginary lines. In consequence, the preventive effect against sideway leakage of body waste in the crotch region 206 is significantly improved.

Figure 8:
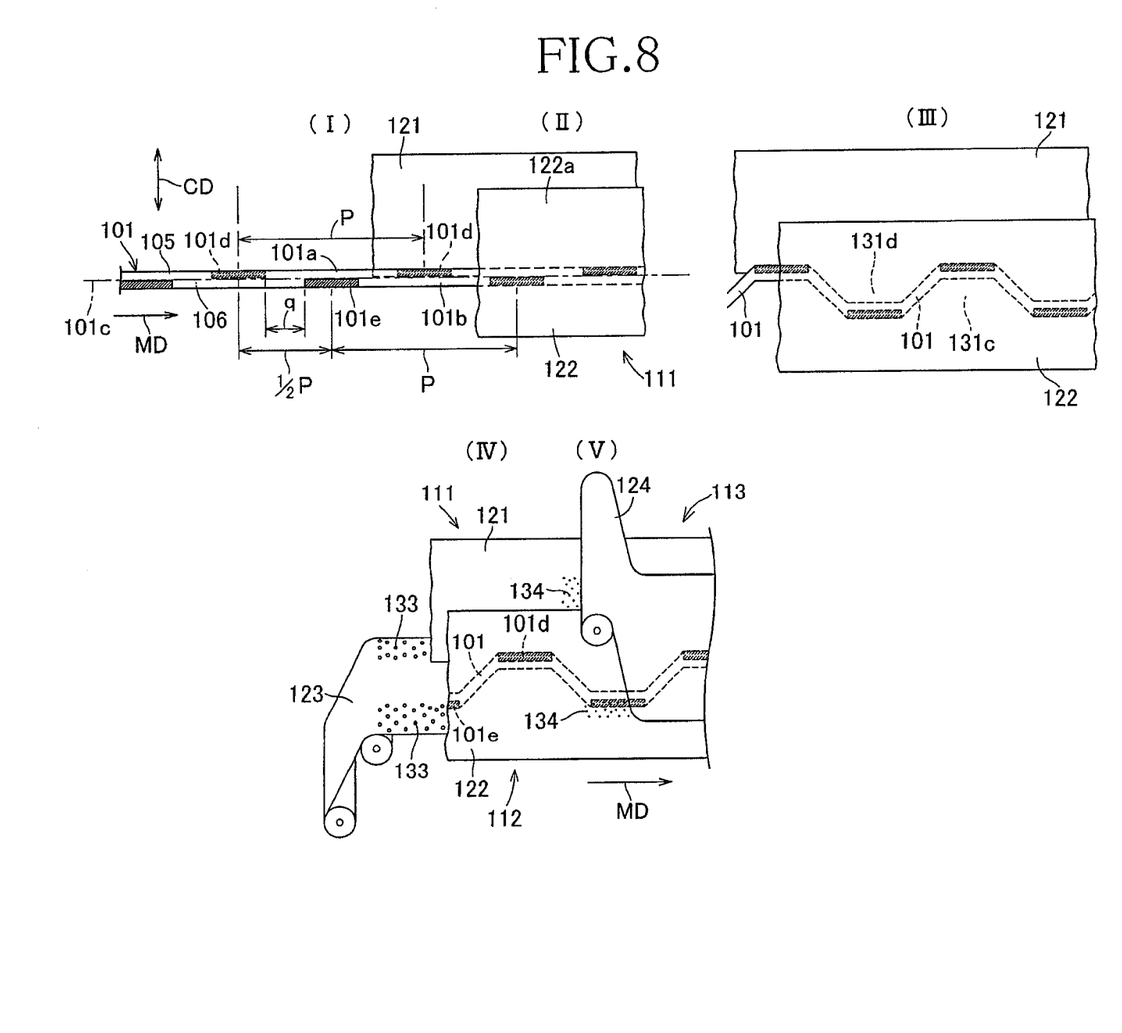
FIG. 8 is a schematic diagram illustrating still another example of the method for making the pants.

FIG. 8 is a schematic diagram illustrating one embodiment of the method according to the present invention, illustrating the steps similar to the first step I through the fifth step V illustrated in FIGS. 4 and 5. In a first step I of FIG. 8, the lower surface 106 of the first elastic web 101 is intermittently, i.e., at intervals p, coated along the first side edge 101a with the first adhesive 101d and then the first inelastic web 121 is continuously fed in the machine direction MD and the inner side edge 121a of the first inelastic web 121 is bonded to the first elastic web 101 by the first adhesive 101d. The first inelastic web 121 has a dimension in the cross direction CD similar to that in FIG. 4 and a sufficient size to define a part of the crotch region 206 and the front waist region 207 of the pants-type diaper 200.

In a second step II, the upper surface 105 of the first elastic web 101 is intermittently, i.e., at intervals p, coated along the second side edge 101b with the second adhesive 101e and then the second inelastic web 122 is continuously fed in the machine direction MD and bonded to the first elastic web 101 by the second adhesive 101e to obtain the first composite web 111. The second inelastic web 122 has a dimension in the cross direction CD, i.e., a width larger than that in FIG. 8 and a sufficient size to define a part of the crotch region 206 and the rear waist region 208 of the pants-type diaper 200 wherein the side edge 122a extends in the cross direction CD so as to overlap the first inelastic web 121. The second inelastic web 122 does not overlap the first adhesive 101d applied to the lower surface 106 of the first elastic web 101.

In a third step III, the first inelastic web 121 and the second inelastic web 122 constituting the first composite web 111 are held and pulled in the cross direction CD. The first elastic member 101 is deformed so as to extend in the machine direction MD in a zigzag pattern. Between the first elastic member 101 and the first inelastic web 121, portions 131c and 131d corresponding to the apertures 131a and 131b formed in the third step III of FIG. 4 are formed. It should be understood that these portions 131c, 131d are concealed by the second inelastic web 122.

In a fourth step IV, the third inelastic web 123 is continuously fed in the machine direction MD and bonded to the first and second inelastic webs 121, 122, preferably also to the first elastic web 101 by the third adhesive 133. In this way, the second composite web 112 is obtained. A dimension of the third inelastic web 123 as measured in the cross direction CD is adjusted so as to cover at least the first elastic web 101 of the broadened first composite web 111.

In a fifth step V, just as in the fifth step V of FIG. 5, the fourth inelastic web 124 is continuously fed in the machine direction MD and bonded to the first and second inelastic webs 121, 122 by the fourth adhesive 134 so that the first and second inelastic webs 121, 122 may be sandwiched between the fourth inelastic web 124 and the third inelastic web 123 to obtain the third composite web 113. The third composite web 113 is subjected to the same steps as the sixth and the subsequent steps illustrated by FIG. 4 to obtain the pants 1.

In the pants 1 obtained by the process illustrated by FIG. 8, the intermediate segments 234 of the leg member 230 obtained from the first elastic web 101 are left free from the second inelastic web 122 defining the crotch region 206. With such pants-type diaper 200, even if the intermediate segments 234 are stretched or contracted during use of the pants-type diaper 200, irritation experienced by the wearer's legs can be alleviated in comparison to the case in which the intermediate segments 234 and the second inelastic web 122 are bonded together by adhesive.

Of the process according to the present invention, the steps illustrated by FIG. 8 may be modified as will be described below. The upper surface 105 of the first elastic web 101 may be coated with the first adhesive 101d and the first inelastic web 121 may be bonded to the upper surface 105. Then, the upper surface 105 may be coated with the second adhesive 101e and the second inelastic web 122 is bonded to the upper surface 105 as seen in FIG. 12 to obtain the first composite web 111. The first composite web 111 obtained in this manner may be subjected to the third step III and the subsequent steps in the same manner as the first composite web 111 of FIG. 8 is processed.

The invention claimed is:

1. A disposable pants-type wearing article having a front-to-rear direction, a transverse direction and a longitudinal direction being orthogonal one to another, said wearing article comprising:
a crotch region,
a front waist region extending forward from the crotch region;
a rear waist region extending rearward from the crotch region, said front and rear waist regions cooperating together to define a waist-opening while said front and rear waist regions cooperate with said crotch region to define a pair of leg-openings; and
an elastic member configured to cause respective peripheral edges of said leg-openings elastically stretchable and contractible in circumferential directions of the respective leg-openings,
wherein
said elastic member comprises a belt having a width in a range of 5 to 60 mm,
said belt includes
leg-contacting segments each extending from a bottom of one of said leg-openings to a top of said leg-opening for surrounding a half of each of a wearer's legs in use, and
a middle segment extending on said bottom across said crotch region to connect respective said leg-contacting segments, and
the leg-contacting segments include
end segments lying on respective said tops of said leg-openings and fixed to a sheet material constituting said wearing article, said middle segment being fixed to said sheet material constituting said wearing article in said crotch region, and
intermediate segments defined between said end segments and said middle segments, and being free to be stretched and contracted,
wherein said belt is in at least one of states selected from the group consisting of:
each said intermediate segment is neither joined nor bonded to said sheet material;
said belt is bonded to said sheet material constituting said wearing article by hot melt adhesive and an application amount of said hot melt adhesive per unit area of said belt is higher in said end segments and said middle segment than in said intermediate segments; and
said front waist region and said rear waist region have joint zones where the waist regions are put flat and welded together, the joint zones extending along opposite side edges of said wearing article, said end segments of said belt extend and are welded to said joint zones by hot melt adhesive, and an application amount per unit area of said hot melt adhesive used to bond said belt and said sheet material to each other is higher in said middle segment than in said intermediate segments.

2. The wearing article according to claim 1, wherein said belt has said end segments and said middle segment fixed to said sheet material in such a manner that said end segments and said middle segment are free of contract.

3. The wearing article according to claim 1, wherein said front and rear waist regions are elastically stretchable and contractible in said transverse direction in the vicinity of respective said tops of said leg-openings.

4. The wearing article according to claim 1, further comprising a bodily fluid absorbent structure extending in said front-to-rear direction on an inner side of the crotch region,
wherein said bodily fluid absorbent structure includes
opposite side edges extending in said front-to-rear direction, and
leak-proof barriers along the opposite side edges and elastically stretchable and contractible in said front-to-rear direction, and said leakage barriers raise themselves to beyond a top surface of said bodily fluid absorbent structure so as to prevent bodily fluids from leaking out through said leg-openings in use.

5. The wearing article according to claim 1, wherein said leg-contacting segments in said belt include:
a front leg-contacting segment extending, in a front half of said crotch region, from said middle segment along the periphery of said leg-opening to said top, and
a rear leg-contacting segment extending, in a rear half of said crotch region, from said middle segment along the periphery of said leg-opening to said top.

6. A method of continuously making a disposable pants-type wearing article as defined by claim 1, in a machine direction and a cross direction orthogonal to said machine direction, said method comprising the steps of:
continuously feeding, in said machine direction, a first elastic web elastically stretchable and contractible in said machine direction, and said first elastic web having upper and lower surfaces extending in said machine direction in parallel to each other as well as first and second side edges extending in said machine direction in parallel to each other, said first elastic web having a width defined between said first and second side edges, said width being a dimension in said cross direction in a range of 6 to 60 mm;
coating one of said upper and lower surfaces with first adhesive zones intermittently in a predetermined cycle;
coating the other one of said upper and lower surfaces with second adhesive zones intermittently in the same predetermined cycle but with a shift of half the cycle, wherein each of said second adhesive zones is spaced from an adjacent one of said first adhesive zones by a predetermined distance as measured in said machine direction, and a total dimension of said adjacent first and second adhesive zones as measured in said cross direction does not exceed the width of said first elastic web;
continuously feeding a first inelastic web having upper and lower surfaces together with a second inelastic web having upper and lower surfaces in said machine direction, then placing one of said upper and lower surfaces of said first inelastic web in contact with said first adhesive zones, but not in contact with said second adhesive zones, to bond said first inelastic web to said first elastic web while placing one of said upper and lower surfaces of said second inelastic web in contact with said second adhesive zones but not in contact with said first adhesive zones to bond said second inelastic web to said first elastic web and thereby to obtain a first composite web;
broadening said first composite web in said cross direction with said first and second inelastic webs being held and thereby elastically stretching said first elastic web between adjacent said first and second adhesive zones in said cross direction;
continuously feeding, in said machine direction, a third inelastic web having a dimension in said cross direction larger than the dimension by which adjacent said first and second adhesive zones are spaced from each other in said cross direction, and placing and bonding upper and lower surfaces of the third inelastic web on and to said first inelastic web and said second inelastic web and thereby to obtain a second composite web;

continuously feeding, in said machine direction, a second elastic web being elastically stretchable and contractible in said machine direction and having upper and lower surfaces, and bonding one of said upper and lower surfaces of said second elastic web under tension to said second inelastic web to obtain a third composite web;

cutting said third composite web along an annular guide line being symmetric about a first center line extending in said cross direction so as to bisect a dimension between adjacent first adhesive zones, the guide line extending along said first elastic web on both sides of said first center line and further extending in said cross direction across a second center line to obtain a fourth composite web;

folding back said fourth composite web along said second center line;

forming said fourth composite web with a joint line so that respective halves of said fourth composite web having been folded back are joined or bonded to each other along said first center line; and cutting said fourth composite web having been folded in said respective halves which have been bonded to each other along said joint line to obtain individual pants-type wearing articles from said fourth composite web.

7. The method according to claim 6, further including, before or after said step of cutting said third composite web, the step of bonding a bodily fluid absorbent structure comprising a bodily fluid absorbent core sandwiched between a liquid-pervious sheet and a liquid-impervious sheet to said third composite web in a manner that said liquid-impervious sheet faces said third composite web.

8. The method according to claim 6, further comprising the step of coating one of said upper and lower surfaces of said first elastic web with both said first adhesive zones and said second adhesive zones.

9. The method according to claim 6, wherein one of said first and second inelastic webs has a width broadened in said cross direction across said first adhesive zones and said second adhesive zones in said first composite web after broadened, and said third inelastic web lying opposite to said first and second inelastic webs.

10. The method according to claim 6, wherein said step of broadening said first composite web in said cross direction with said first and second inelastic webs being held comprises pulling the first composite web in said cross direction so that said first and second inelastic web are spaced away from each other in said cross direction to define the first elastic web in a zigzag pattern and a plurality of apertures alternatingly arranged with the first and second adhesive zones in the machine direction.

11. The method according to claim 6, wherein the second inelastic web is applied onto the first inelastic web so that the second inelastic web overlaps the first inelastic web.

* * * * *